US008291745B2

(12) United States Patent
Karabacak et al.

(10) Patent No.: US 8,291,745 B2
(45) Date of Patent: Oct. 23, 2012

(54) ANALYTE SENSING DEVICE

(75) Inventors: Devrez Mehmet Karabacak, Eindhoven (NL); Koray Karakaya, Eindhoven (NL)

(73) Assignee: Stichting IMEC Nederland, Eindhoven (NL)

(*) Notice: Subject to any disclaimer, the term of this patent is extended or adjusted under 35 U.S.C. 154(b) by 492 days.

(21) Appl. No.: 12/495,451

(22) Filed: Jun. 30, 2009

(65) Prior Publication Data
US 2010/0000292 A1 Jan. 7, 2010

Related U.S. Application Data

(60) Provisional application No. 61/077,825, filed on Jul. 2, 2008.

(51) Int. Cl.
G01N 7/00 (2006.01)
G01N 5/02 (2006.01)
G01N 9/00 (2006.01)
G01N 29/02 (2006.01)

(52) U.S. Cl. .................. 73/24.01; 73/24.06
(58) Field of Classification Search ............. 73/23.34, 73/24.01, 24.03, 24.05, 24.06
See application file for complete search history.

(56) References Cited

U.S. PATENT DOCUMENTS

| | | | |
|---|---|---|---|
| 3,879,992 A * | 4/1975 | Bartera | 73/24.01 |
| 4,361,026 A * | 11/1982 | Muller et al. | 73/24.01 |
| 5,321,331 A * | 6/1994 | Baer et al. | 73/24.01 |
| 5,719,324 A | 2/1998 | Thundat et al. | |
| 5,756,279 A * | 5/1998 | Ebersole et al. | 422/68.1 |
| 6,722,200 B2 * | 4/2004 | Roukes et al. | 73/580 |
| 6,955,787 B1 * | 10/2005 | Hanson | 422/50 |
| 7,178,378 B2 * | 2/2007 | Crawley et al. | 73/24.06 |
| 7,395,698 B2 * | 7/2008 | Degertekin | 73/105 |
| 7,409,851 B2 * | 8/2008 | Ilic et al. | 73/24.06 |
| 7,500,379 B2 * | 3/2009 | Hines | 73/24.06 |
| 7,555,938 B2 * | 7/2009 | Bargatin et al. | 73/64.53 |
| 7,770,449 B2 * | 8/2010 | Chen et al. | 73/335.05 |
| 7,854,159 B2 * | 12/2010 | Gerlach et al. | 73/61.41 |
| 7,886,575 B2 * | 2/2011 | Haskell et al. | 73/24.01 |

(Continued)

FOREIGN PATENT DOCUMENTS
WO WO 2007/030240 3/2007

OTHER PUBLICATIONS

Snow et al., "Static deflection measurements of cantilever arrays reveal polymer film expansion and contraction", Journal of Colloid and Interface Science, vol. 316, pp. 687-693, Aug. 30, 2007.
Jun et al., "Electrothermal tuning of Al-SiC nanomechanical resonators", Nanotechnology, vol. 17, No. 5, pp. 1506-1511, Feb. 16, 2006.
Li et al., "Ultra-sensitive NEMS-based cantilevers for sensing, scanned probe and very high-frequency applications", Nature Nanotechnology, vol. 2, pp. 114-160, Feb. 2007.

(Continued)

Primary Examiner — Lisa Caputo
Assistant Examiner — Punam Roy
(74) Attorney, Agent, or Firm — Knobbe Martens Olson & Bear LLP

(57) ABSTRACT

A sensing device for detecting an analyte is disclosed. In one aspect, the device includes at least one geometrical structure and at least two clamps provided for clamping the at least one geometrical structure on at least two ends of the geometrical structure. The at least one geometrical structure has at least one chemical responsive layer being absorbent or adsorbent for the analyte, and a support structure provided for at least partly supporting the at least one chemical responsive layer. The at least one chemical responsive layer has a varying effective spring constant which changes upon absorption or adsorption of the analyte.

18 Claims, 9 Drawing Sheets

U.S. PATENT DOCUMENTS

2004/0016287 A1* 1/2004 Fu .................................. 73/23.34
2009/0284102 A1* 11/2009 Karakaya et al. .............. 310/321
2009/0293590 A1* 12/2009 Zeng et al. .................... 73/24.06
2010/0233792 A1* 9/2010 Begley et al. ............... 435/287.1

OTHER PUBLICATIONS

Schroth et al., "A resonant poliyimide-based humidity sensor", Sensors and Actuators B, vol. 34, pp. 301-304, Jun. 1996.

\* cited by examiner

ANALYTE SENSING DEVICE

CROSS REFERENCE TO RELATED APPLICATIONS

This application claims priority under 35 U.S.C. §119(e) to U.S. provisional patent application 61/077,825 filed on Jul. 2, 2008, which application is hereby incorporated by reference in its entirety.

BACKGROUND OF THE INVENTION

1. Field of the Invention

The present invention relates to a sensor for sensing analytes, and more specifically to a micro/nanomechanical sensor.

2. Description of the Related Technology

In WO2007/030240, Begley et. al. describe the use of doubly-clamped beams or membrane for the detection of chemical and biological material by generating stress induced static deformations. It relies on surface stress formation due to surface binding of biomolecules. However, the formation of this stress requires large molecules, preferably electrically-charged, to be closely-packed upon the surface so that there are repulsive/attractive interactions. As a result, there are significant limitations in the application of this technique to high-precision gas sensing which involves small, uncharged molecules at low concentrations that often do not form a uniform, dense coating through simple binding. Furthermore, the design in WO2007/030240 employs static detection technique, which relies on accurate measurement of miniscule deformations in the proposed structure. The static detection approach provides significantly weak signals even when very soft structures with high aspect ratios (i.e. geometries that are thin and long) are employed. As such, the method is highly restricted in scalability and sensitivity. Moreover, the structure is fully constructed from a flexible material (i.e. polymer), which limits the potential for integrating with silicon-based fabrication methods and actuation/readout components. Additionally, the static approach is often significantly more prone towards external perturbations (i.e. ambient vibrations, noise and drift) which limit both short and long term stability of the transduced signal, reducing the obtainable sensitivity.

In J. of Colloid and Interface Science vol. 316, pg. 687-693 (2007), Snow et. al. attempt to adapt a similar principle to gas sensing by using a cantilever single-side coated with a polymer for gas sensing. The deflection of the cantilever tip due to gas absorption-induced swelling of the polymer layer is optically transduced in a static read-out scheme. The above mentioned limitations of the static approach remain. Furthermore, the response is dependent on obtaining a large differential stress between the two cantilever surfaces, hence only one side can be coated with gas-absorbent coating to obtain optimum performance. Additionally, as with the idea of Begley et. al., the sensitivity of the device relies on the use of a high-aspect ratio (long and thin) cantilevers, which are limited in scalability and sensitivity. To improve these issues, Snow et. al. employ a complex optical readout approach, but this results in a more challenging, high-power transduction mechanism, that is difficult to integrate and multiplex into an array, particularly for low-power requiring wireless autonomous sensor nodes.

M. Li et. al. in Nature Nanotechnology, vol. 2, pg. 114 (2007) try to overcome the limitations of the static approach by employing the cantilever devices in a resonant detection circuit. A polymer coating on the cantilever is used in capturing the difluoroethane gas molecules to generate a mass-induced resonance frequency shift. However, the devices rely simply on mass effect which is often very limited for gas molecules, and detection requires the absorption of a significant number of molecules. The accumulation of the minimum detectable concentration can require a significant response time.

In U.S. Pat. No. 5,719,324, Thundat et. al. claim a cantilever (single-clamped structure) to be responsive to gaseous analytes when single-side of its surface is partially treated for formation of surface tension upon adsorption of the analyte. The vibration characteristics of cantilevers, however, are known to be largely insensitive to stress formation due to their highly flexible nature where the tip is free to deform to relieve stress through strain, and the effect is argued to be less prominent than previously claimed. Furthermore, in the proposed layout, the sensing effect is confined to the surface. As such, the proposed mechanism is highly inefficient approach in coupling the surface stress into a bulk effect in the structure. Since resonance characteristics of the device are determined by changes in its bulk properties, this approach limits resonant sensitivity of the structure. Even then, the surface stress effect is reported to be observable only within a region near the clamp. As such, this approach is highly limited in transduction area and scalability. Additionally, the setup proposed by Thundat et. al. is vibrated by a common actuation transducer which means all vibrations will be at a single frequency at any given time, limiting the possibility of characterizing vibrations from different structures in real-time. Moreover, the detection is performed using complex, high-power requiring optical means where a laser beam is aligned to the tip of each cantilever. The requirement to have individually aligned optical source and detector significantly limits both the size of each cantilever and the number of devices that can be integrated. As such, the sensor proposed in U.S. Pat. No. 5,719,324 is not suitable for gas sensing applications where selectivity can only be achieved by large arrays using differential measurement of individually sensitive devices, particularly when low-power and small form factor requirements exist as in autonomous sensor nodes.

Membranes have also been adapted to gas sensing by A. Schroth et. al. in Sensors and Actuators B, vol. 34, pg. 301-304, (1996), who employed polyimide-coated resonant membrane for detection of humidity. Significant swelling of the polyimide polymer when exposed to humidity and a frequency shift were observed. Membranes, however, due to their geometry, are significantly stiffer than doubly-clamped beams of identical length, thickness and material. Resultantly, the membranes are significantly limited in amplitudes of motion, requiring more power consuming actuation and detection schemes. As such, membrane geometry lacks scalability, requires significantly larger surface areas, and limits the ability to construct arrays of sensor devices in small form factors needed for sensor node applications. The size of the membranes also hinders their resonant operation in fluidic environments since damping effects in membranes will be more pronounced in comparison to the slender design of the beam geometry disclosed in this description. Also, the diffusion of the analyte into a membrane coating can be a slower process, as it typically provides a smaller surface to mass ratio when compared with beam geometry with identical layer thicknesses.

S. C. Jun, X. M. H. Huang, M. Manolidis, C. A. Zorman, M. Mehregany, and J. Hone, (in Nanotechnology, vol. 17, no. 5, pp. 1506-1511, 2006) describe the responsivity of composite doubly-clamped beam resonators to ambient temperature dependent thermally-induced stress effects but its unresponsive analytes of any type.

A need thus remains for sensing devices of low complexity, small size, and high sensitivity for detection of analytes, particularly those with low molecular weight.

SUMMARY OF CERTAIN INVENTIVE ASPECTS

Certain inventive aspects relate to an improved sensor for sensing analytes with higher sensitivity, enhanced selectivity and reduced response time when compared to prior-art sensing devices.

In particular, the sensing device according to one inventive aspect comprises at least one geometrical structure which is clamped on at least two of its ends. In addition, the at least one geometrical structure comprises at least one chemical responsive layer which is absorbent or adsorbent for an analyte and which has a varying effective spring constant that changes upon absorption or adsorption of the specific analyte.

An analysis of the prior art sensing devices has shown that they rely on either cantilever (single clamp) micromechanical structures or membrane structures, where either static deformations or resonance frequency shifts are monitored as an indication of the presence of an analyte. Such existing sensor systems have their drawbacks. Sensor systems based on cantilevers with sorbent polymer coatings clamped at one end only are highly ineffective in converting swelling-induced effects to resonance frequency shifts. The cantilever geometry is not suited to induce stress-formation as the non-clamped end is free to deform, longitudinally or through bending, to release the stress through strain. Also, polymer-coated cantilevers for the gas sensing through static bending measurements require very soft, long cantilevers for creating a detectable bending. As such, the static approach is difficult to scale and shows low sensitivity when scaling or for detecting small amounts of an analyte. Sensors based on a membrane structure have a thin suspended plate with all edges clamped is coated with polyimide. While such membranes can achieve stress accumulation, for example due to water vapor absorption, the geometry of the membrane makes it very stiff, for example when compared to cantilevers of similar length and thickness, which are only clamped at the ends of only single (longitudinal) axis. The stiffness of membranes creates challenges in actuation and detection of their vibrational modes. As a result, membranes are not as scalable as cantilevers. The size of the membranes also hinders their resonant operation in fluidic environments since damping effects in membranes will be more pronounced.

The sensing device solves the above mentioned drawbacks by using the geometrical structure whose peripheral edge is only partially clamped, leaving at least part of its peripheral edge free to vibrate. In comparison to the prior art cantilever sensors, the clamping on opposite sides makes the geometrical structure more suitable for stress accumulation, leading to a much more pronounced change in the resonance mode characteristics. In comparison to the prior art membrane sensors, the partial clamping of the peripheral edge (so not around the whole periphery) significantly reduces the stiffness, resolving the challenges in actuation and detection of the vibrational modes.

Thus, the sensing device relates to a device that allows for sensing molecules, especially small molecule analytes (gas, vapor, small particles), with high sensitivity, enhanced selectivity and reduced response time.

The combination of the specific type of chemical responsive layer used and the multiple clamping of the geometrical structure allows the detection of analytes (gas, vapor, small particles), and in particular analytes with small molecular weight, with high sensitivity, enhanced selectivity and reduced response time.

Absorption or adsorption of an analyte by the chemical responsive layer triggers a change in the effective spring constant, for example as a result of a change in volume of the layer (i.e. swelling/shrinking). The multi-clamped design of the structure restricts the change of volume in one or more layers in at least one axis. This desire of volume change in one or more layers coupled with the restrictions in geometry induces bulk stress within the geometric structure. For example, the clamped-clamped boundary conditions of a suspended beam will cause a compressive (squeezing) stress when one or more layers are triggered to swell upon interaction with an analyte. The induced stress may then be used in the detection of gases as it results in a change in the vibration characteristics. Because the geometric structure is clamped on at least two of its ends, stress-release through strain is reduced significantly, when compared to cantilevers clamped at only one end. As a result, the sensing device allows for a significantly more efficient coupling to resonance frequency shift when compared to cantilevers clamped at only one end. By operating such composite multi-clamped devices in their resonant modes, significant improvements can be obtained over methods that simply rely on structural deformation measurements or inertial effects. An increase of the induced stress results in an enhancement of the detection capabilities for analytes, in particular for analytes of low molecular mass.

The at least one geometrical structure is clamped on at least two ends of the geometrical structure. The at least two ends can be clamped on any two locations of the geometric structure taken in height or width direction of the geometric structure or at two other locations of the geometric structure. Preferably, the geometric structure is clamped on at least two opposite ends of the geometric structure, because this results in an increase of the induced stress upon absorption or adsorption of an analyte. More preferably, the geometric structure is clamped on at least two opposite ends of its principal axis because this results in a maximal induced stress, and thus in an enhanced detection of an analyte by the sensing device.

In preferred embodiments, the geometrical structure has at least one main axis and is exclusively clamped on opposite ends of the at least one main axis, such that most of the peripheral edge is left free to vibrate. An example of such a structure is a doubly-clamped beam, which is as scalable as the prior art cantilever structures.

The at least one chemically responsive layer can be volume-responsive, meaning that the volume of the layer will change upon absorption and adsorption of an analyte. Preferably, the volume increases upon absorption of an analyte and the volume decreases upon adsorption of an analyte. The at least one chemical responsive layer can be chosen from a range of materials that demonstrate a volume change response upon absorption or adsorption of a specific analyte. Because the geometrical structure is clamped on at least two ends, the volume change upon absorption or adsorption of the specific analyte, will result in a strong stress formation in the geometric structure upon absorption or adsorption of the specific analyte.

Preferably, the geometric structure has a high-aspect ratio where the relevant aspect ratio for the proposed device can be defined as the ratio of the length of the geometric structure to its thickness. The aspect ratio is often limited by the fabrication capabilities, device fragility or geometric constraints, but aspect ratio (length/thickness) values between 10 and 2000 can be obtained using established microfabrication techniques. A high aspect ratio is advantageous for increased resonance responsivity. The resonance responsivity can be defined as the obtained change in the resonance characteristics of the device per amount (concentration) of the analyte in its environment. The overall detectable analyte concentration will also depend on the nominal resonance frequency of the mode of operation geometric device, as well as the read-out circuit, and therefore may require further geometric optimization.

Optionally, or in addition to the volume-response of the at least one chemical responsive layer, the flexural rigidity, i.e. the stiffness, of the at least one chemical responsive layer can change during absorption or adsorption of an analyte, which will change the effective flexural stiffness of the structure, and thus an enhanced (increased) resonance responsivity.

Optionally, or in addition to the volume-response and/or the rigidity-response, the mass of the at least one chemical responsive layer can change during absorption or adsorption of an analyte, which will again induce a resonance frequency shift for the structure, and thus an enhanced resonance responsivity.

In another embodiment, repulsive/attractive forces within the adsorbed or absorbed layer can create surface stress, and thus an enhanced response signal.

Also exothermic/endothermic reactions within one or more layers leading to a temperature increase/decrease can result in a change of the volume and/or elasticity. This effect can also be used as the sensing or identification mechanism for one or more analytes. However, the thermal responsivity of the composite structure can also result in an undesired interference into the absorption-induced response. This interference, which exists in many prior-art sensing devices, is often cancelled out by signal analysis using temperature data from a separate sensor element (e.g. thermocouple, thermistor) that is integrated into the sensor device. However, such separate measurement approach can result in power consuming data analysis algorithms. The proposed sensing device here, however, allows for the removal of such non-analyte related effects through its arrayability where multiple versions of the above described device can be integrated next to each other to perform differential read-out as described below.

In one aspect, summarizing one or more absorption-induced physical effects (i.e. change(s) in volume, mass, temperature, flexural rigidity etc.) in at least one structural layer are expected to result in a change in the resonance mode characteristics of at least one vibrational mode of the geometric structure. Most importantly, the bulk stress formation induced within the structure due to for example volume effects (swelling/shrinking) of one or more layers is significantly higher compared to structures which are only clamped at one end, enhancing the sensitivity and responsivity of the sensing device. Preferably, the response of the structure to physical or chemical interaction with its environment is simultaneously the result of multiple effects, for instance a volume change in combination with a rigidity change and/or mass change, enhancing the sensitivity and responsivity of the sensing device.

The at least one geometrical structure can further be designed to be resonantly operated. Changes in resonance mode characteristics of the geometric structure can be monitored actively or passively in one or more resonance modes, as an indication of chemical/physical interaction with fluidic substances in the vicinity of the device. These changes can be in the form of frequency shift, amplitude change and/or quality factor (bandwidth) variations. The changes in resonance characteristics of the mode(s) may for instance be the result of changes in the volume of the chemical responsive layer upon absorption of an analyte, which due to the clamping at several locations will restrict static formation of the structure and will consequently result in a bulk stress formation in the chemically responsive layer. Furthermore, the mass of the chemically responsive layer will increase upon absorption of an analyte. Both changes in mass and stress may for example have an influence on the resonance frequency of the geometric structure. The use of the multi-clamped resonator geometry and integration of volume-responsive layering allows for the simultaneous and combined measurement of both changes. As a result, the absorption process will generate a measurable resonance frequency shift. An enhancement is obtained by exploiting the stress-induced resonance effect on top of the mass-induced resonance frequency shifts. The proposed design as such increases the responsivity and sensitivity of sensors without adding significant complexity to the geometry.

The design of the resonator and the selection of materials allow for the optimization of the response time, amplitude and selectivity towards gas molecules depending on the requirements of the application. Additionally, certain inventive aspects reduce the size limitations of similar systems, facilitating large arrays of uniquely coated sensing elements to be constructed in small form factors. Such arrays can then be employed in extracting simultaneous measurements of analyte sorption to different sensor coatings, improving the selectivity of such devices to certain gases in complex mixtures.

Time resolved tracking of the changes in the resonance characteristics of individual device or a group of devices can also be performed to extract transient characteristics of the chemophysical interaction which are determined by different time constants (for example diffusion time, material relaxation time, thermal time constants), whose combination often provides a unique response signature for each analyte-absorbent material pairing. Such time-resolved information can be used as an additional source to obtain selectivity between different analytes present in the ambient.

Optimization of the composite structuring can be done, such that, depending on the characteristics of the materials used in the layers, the stress-induced response can be amplified by varying layer thicknesses. As a result, the system can be tuned to be highly responsive towards analytes with small molecular mass, which are typically very difficult to detect rapidly at low concentrations using prior integrated techniques. Furthermore, the enhanced response of the resonator simplifies the requirements on the actuation/detection subsystems allowing for low-power, scalable and integratable approaches to be implemented. So the proposed design is scalable, tunable and can be integrated with other functionalities.

The at least one chemical responsive layer can be a layer (e.g. polymer, (hydro)gels, dendrimers, polyelectrolyte multilayers, or ionic liquids) with affinity for analytes (gas, vapor, particle etc.) to be measured. The material of the polymer can be chosen such that it adsorbs specific gases. Preferably, appropriate chemistry can be selected such that the absorption of the target molecules from the ambient will lead to both a mass and volume change in the chemically responsive layer. For the chemical responsive layer the following materials can be used: polyvinyl chloride (PVC), polyvinyl butyral (PVB), polyvinyl acetate (PVA), polyetherurethane (PEUT), poly (methyl methacrylate) (PMMA), polyvinylpyridine (PVP) and polyimide, among others, or room temperature ionic liquids like [p5mim][bFAP], among others, or polyelectrolyte multilayers (PEM) such as poly(styrene sulfonate)

(PSS)/poly(diallyldimethylammonium chloride) (PDADMAC) among others. The chemical responsive layer can be chosen depending on the chemistry of the analyte that needs to be detected. The selection of the polymer can be based on application and the desire to optimize the absorptivity, selectivity, swelling response or response time towards a specific analyte. For example, for detection of octane vapors, PEUT composites can be % employed, or measurement of water vapor presence could be achieved using PVP layers. Polymer swelling due to absorption has been demonstrated for example for polysiloxane upon exposure to hydrocarbon vapors, polyiso-butylene (PIB) and polyethylene-vinyl-acetate (PEVA) upon exposure to hexane and toluene, polyvinylalcohol (PVA) upon exposure to methanol and isopropanol, and polyimide upon exposure to humidity.

Room temperature ionic liquids, sometimes referred to as molten salts, are also known to be selectively absorbent towards vapors (e.g. [p5mim][bFAP] for $CO_2$). Ionic liquids intrinsically very low vapor pressure and tailored viscosity make them suitable candidates as durable coating materials on the proposed sensor elements. Furthermore, ionic liquids are known to be volume-responsive (often swelling) upon absorption of vapor analytes, among other changes in their mechanical properties. The coating of ionic liquids onto the suspended structures can be achieved by standard methods like inkjet printing, spraying, dipping or spin coating, upon dilution in an appropriate solvent if necessary, in a manner similar to polymer deposition techniques.

The support structure of the sensing device can be structured at its interface(s) with the chemical responsive layer(s) with microscale and/or sub-microscale grooves or holes being etched into the support structure. The etched areas can be subsequently filled, either partially or completely, with material of the chemical responsive layer. As a consequence, the effective spring constant change of the material in the grooves (holes) resulting for instance from a volume change of the material upon absorption/adsorption of an analyte from the environment can result in a more prominent formation of structural stress and a more pronounced resonance frequency shift response of the sensor element. The location of the grooves can be selected to generate stress in specific locations or can be distributed through-out the structure.

The grooves can be aligned to any direction, but will be preferably perpendicular to the clamping direction, i.e. the direction in which the geometrical structure is clamped, to ensure the greatest stress formation in this direction. The holes can be of any shape or size and can be patterned into the structure using chemical (wet or dry) etching with or without lithographic patterning or using physical etching techniques like focused ion beam (FIB). The depth of the etched structure will be less than the thickness of the structural layer, but can be varied to ensure either a complete filling of the etched region by the volume-responsive coating or partial filling. Alternatively, the surface structure can be created bottom-up deposited using techniques like atomic layer deposition (ALD), or growth techniques etc.

The sensing device can contain embedded actuation and detection sub-systems. The actuation and detection mechanisms can be a combination of piezoelectric, piezoresistive, thermal or optical components. The multiple-clamped geometry allows for the separation of actuation and detection mechanisms by placing each one at another clamping area. The design also allows for separation of the transduction mechanisms and their electrical connections from the analyte sensitive region, minimizing any undesired interference between the chemophysical reaction and its detection.

The sensing device(s) can also contain integrated heating/cooling elements (e.g. resistive heaters, thermoelectric layers), such that the temperature of individual resonators can be adjusted to promote absorption or desorption of the analyte(s) or to maintain the sensing device(s) at constant temperature. Owing to the size of the sensing device, the thermal capacity will be minimal and will allow for rapid thermal cycling and low-power operation.

BRIEF DESCRIPTION OF THE DRAWINGS

The invention will be further elucidated by means of the following description and the appended drawings.

FIG. 6($b$) shows the piezoelectric patch of the device described in FIG. 6($a$) biased with varying dc voltage.

DETAILED DESCRIPTION OF CERTAIN ILLUSTRATIVE EMBODIMENTS

Figure 1A:
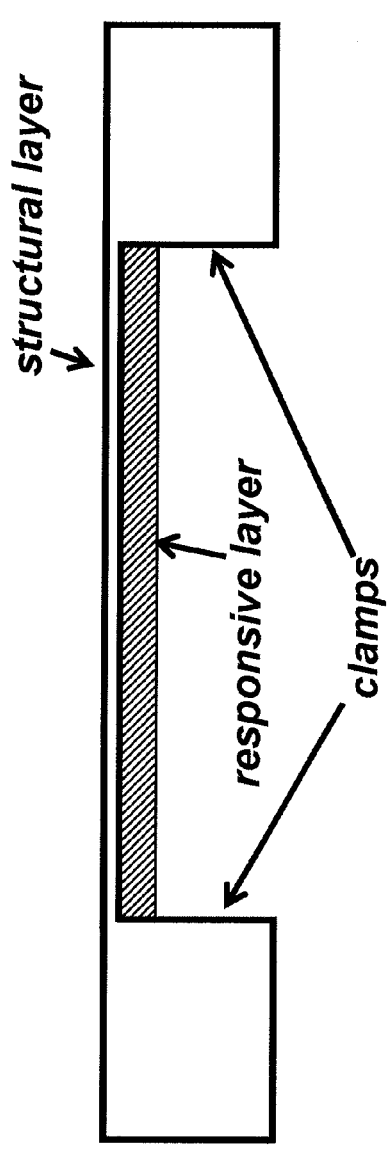
FIG. 1 shows a cross-sectional view of (a) a first embodiment of the sensing device according to the invention comprising a bi-layered beam-shaped geometric structure, and (b) a second embodiment of the sensing device according to the invention comprising a tri-layered beam-shaped geometric structure.

The present invention is described with respect to particular embodiments and with reference to certain drawings, but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third, and the like in the description and in the claims, are used for distinguishing between similar elements and not necessarily for describing a sequential or chronological order. The terms are interchangeable under appropriate circumstances and the embodiments of the invention can operate in other sequences than those described or illustrated herein.

Moreover, the terms top, bottom, over, under, and the like in the description and the claims are used for descriptive purposes and not necessarily for describing relative positions. The terms so used are interchangeable under appropriate circumstances and that the embodiments of the invention described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

It should be understood that the illustrated embodiments are examples only and should not be taken as limiting the scope of the present invention. The claims should not be read as limited to the described order or elements unless stated to that effect. Therefore, all embodiments that come within the scope and spirit of the following claims and equivalents thereto are claimed as the invention.

As used herein, with "analyte" is intended to mean the substance of interest whose presence or concentration is to be detected by the sensing device.

With "resonance mode characteristics" is intended the vibrational behavior (e.g. resonance frequency, quality factor, mode shape) of the geometric structure for a given natural mode of vibration.

With "resonance responsivity" is intended the amount of change in the vibrational characteristics (resonance frequency, quality factor etc.) of the geometric structure for a given natural mode of vibration, per amount of analyte present in the device vicinity.

FIGS. 1a-1b, 2 and 4a-4c show different embodiments of a sensing device.

Figure 1B:
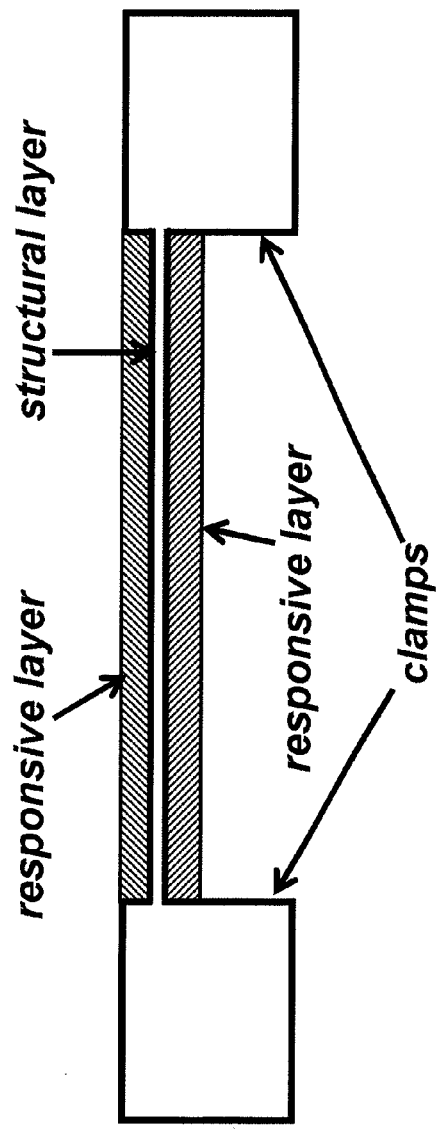
Figure 4A:
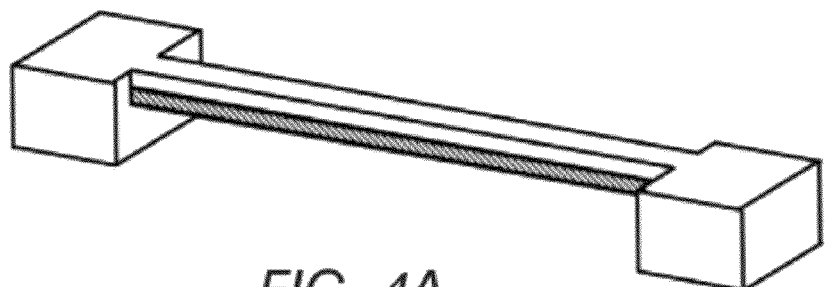
FIG. 4 shows a fundamental mode sketch of (a) a single doubly-clamped composite suspended beam, (b) a composite cross-beam resonator clamped at four ends and (c) a doubly clamped H-resonator.

The sensing device shown in FIGS. 1a-1b and 4a comprises a beam-shaped geometric structure clamped at two ends of its longitudinal axis by two clamps. By restricting the length of the geometric structure at both of its ends, the stress accumulates in its principal longitudinal axis when one or more of the chemical responsive layers experiences a change in volume, upon absorption or adsorption of an analyte. The stressed-state of the doubly-clamped beam results in a resonance frequency shift in the fundamental vibrational mode, as well as the higher order harmonic modes of the device. This stress-induced resonance frequency shift can be in addition to a mass-induced effect on the resonance characteristics. As such, the responsivity and the sensitivity of the device can be significantly enhanced and the response time can be reduced. Additional frequency shifts can occur due to structural rigidity change (stiffening/softening) in one or more layers and such changes can be utilized to further enhance the response of the sensing device.

The amount of induced stress depends on layer thicknesses, device geometry, material rigidities of the geometric structure and the amount of volume change.

Alternatively, the beam-shaped geometric structure, and more in general the geometric structure, may be clamped at two opposite ends of the geometric structure taken in height or width direction of the geometric structure or at two other locations of the geometric structure. However, clamping the geometric structure at two ends of its principal axis, i.e. its longitudinal axis in case of a beam-shaped structure, is preferred because it results in a maximal stress-induced resonance frequency shift, and thus in an enhanced detection of an analyte by the sensing device.

The geometric structure shown in FIGS. 1a and 4a is a two layered structure comprising one support structure and one chemical responsive layer provided on the bottom side of the support structure. The geometric structure shown in FIG. 1b is a three layered structure comprising one support structure and two chemical responsive layers provided on opposite sides of the support structure. Unlike cantilevers which are clamped at only one end and which provide no stress formation when coated on both sides, the doubly-clamped beam response will be enhanced when constructed from multiple responsive layers. The chemical response layers shown in FIGS. 1a, 1b and 4a completely cover the bottom and/or top side of the support structure. Alternatively, the chemical response layer may cover only part of the bottom and/or top sides of the support structure. Thereto, the supporting structure can for instance be totally or partially coated with an absorbent material (polymer, gels or other) or possessing a molecular binding site, such that absorption/adsorption will result in one or more of mass change, stiffness change, enthalpy change, stress accumulation or thermal effect in the structure.

When the sensing device comprises multiple chemical responsive layers, such as for instance in the 3-layered structure shown in FIG. 1b, the chemical responsive layers can be the identical or different. The chemical responsive layers can be chosen to be responsive for different analytes, can be chosen to have a varying thicknesses or lengths, to provide the sensing device with additional responsivity and/or selectivity.

Figure 4B:
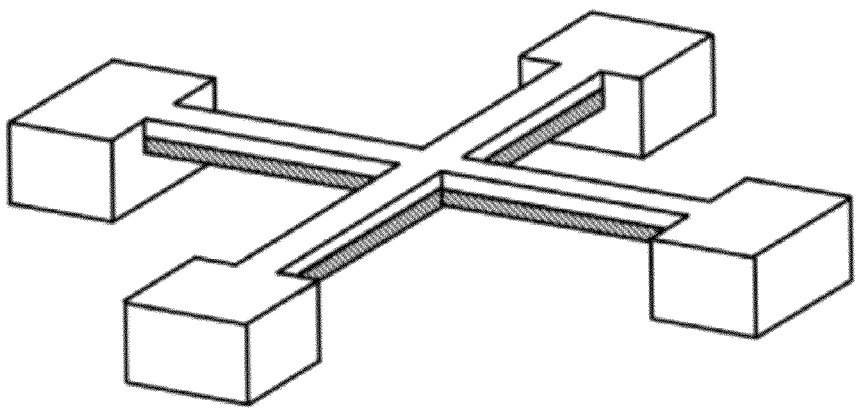
Figure 4C:
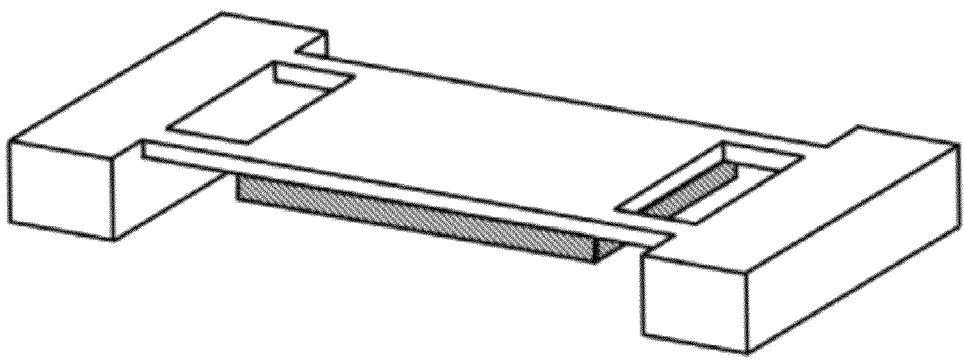

A beam-shaped geometric structure has the advantage that it only takes a minimum amount of space, allowing the structure to be used in array structures comprising a number of geometric structures one next to the other. The cross section of the beam-shaped structure may have any shape considered suitable by the person skilled in the art such as square, rectangular, circular or trapezoidal. However, other shapes than the beam shape can be used for the geometric structure. The geometric structure may have any shape considered suitable by the person skilled in the art. Some other examples of geometries are represented in FIGS. 4b-4c. A composite cross-shaped resonator is for instance shown in FIG. 4b. Such a structure may yield a similar effect with possibly a larger responsivity, albeit with larger area coverage. FIG. 4c shows an H-shaped geometric structure formed by suspended coupled beams, clamped on at least two ends. The composite sensor element is suspended by flexible supports as is shown in FIG. 4c such that variations in different resonance modes are individually more susceptible to stress formation or inertial loading. As such, simultaneous multi-mode detection can be performed to extract additional sensor data.

The support structure of the sensing device is provided for at least partly supporting the at least one chemical responsive layer. The support structure can be used for enhanced rigidity, robustness and to obtain more desired resonance characteristics like high resonance frequency, high quality factor (low structural dissipation). The support structure can for instance be fabricated from materials like silicon, silicon dioxide, silicon nitride, gallium arsenide and their composites, having a flexural rigidity (modulus of elasticity) above 50 GPa. These materials are also suitable due to their availability in very pure form with very few defects and impurities, which allows for low structural dissipation to occur during resonant operation, resulting in very high mechanical quality factors to be obtained (up to 106 in vacuum and above 100 in air). Desired resonance frequencies can be in the range of 1 kHz to 100 MHz.

The width of the beam-shaped structure, and in general of the geometric structure, can vary between 1 μm and 100 μm. For the a uniform cross-section doubly-clamped beam, the width has little impact on the responsivity but will affect the amplitude of vibration, actuation power and response time. The responsivity of other embodiments, like those shown in FIG. 4b-c, as well as the higher modes of non-uniform cross-section beams, will be also strongly dependent on the width.

The thicknesses of the different layers and their ratio is significant in determining the characteristics of the sensing device response to the analyte presence, allowing them to be tuned to achieve maximum frequency shift, quickest response time and desired selectivity. The thicknesses of the support structure and the at least one chemical responsive layer can range from 100 nm up to few microns. The ratio of the two thicknesses can be optimized to achieve best response depending on the characteristics of the layer materials (e.g. modulus of elasticity and density). Preferably, the absorption layer should be about twice as thick as the structural layer when the absorption layer is about two orders of magnitude softer than the structural material.

The length of the geometric structure can also be varied to achieve desired resonance frequency and responsivity, and it can typically range between 5 μm and 500 μm. Most significantly, the responsivity of the resonator is found to be independent of length and dependent on the length to thickness aspect ratio, which makes the embodiment(s) scalable without loss of performance. Preferably, the aspect ratio should be as high as possible, with values above 100 being feasible to fabricate and operate.

The resonance frequency without load can vary between kHz level and 100 MHz. Upon gas absorption, the resonance frequency can shift up to 10% per 0.1% swelling. Such a level of swelling (~0.1%) can be obtained even in the presence of ppb-level analyte concentrations when the appropriate absorbent material is selected. The responsivity level of the proposed sensor (~100:1) is significantly higher than other methods that rely on layer thickness change (i.e. capacitive, static bending). As such, the multi-clamped composite resonators allow for ppb-level analyte detection sensitivities to be achieved, even for particles of small molecular weight.

The chemically responsive (e.g. polymer or ionic liquid) section can be restricted in length along its principle axis, such that a volumetric change triggered by a physical, chemical or biological effect leads into a stress formation, and resulting in a frequency shift for one or more vibrational resonance modes. The chemically responsive section can also consist of a stack of multiple layers to optimize responsivity, selectivity and/or response time as desired for one or more analytes.

Figure 2:
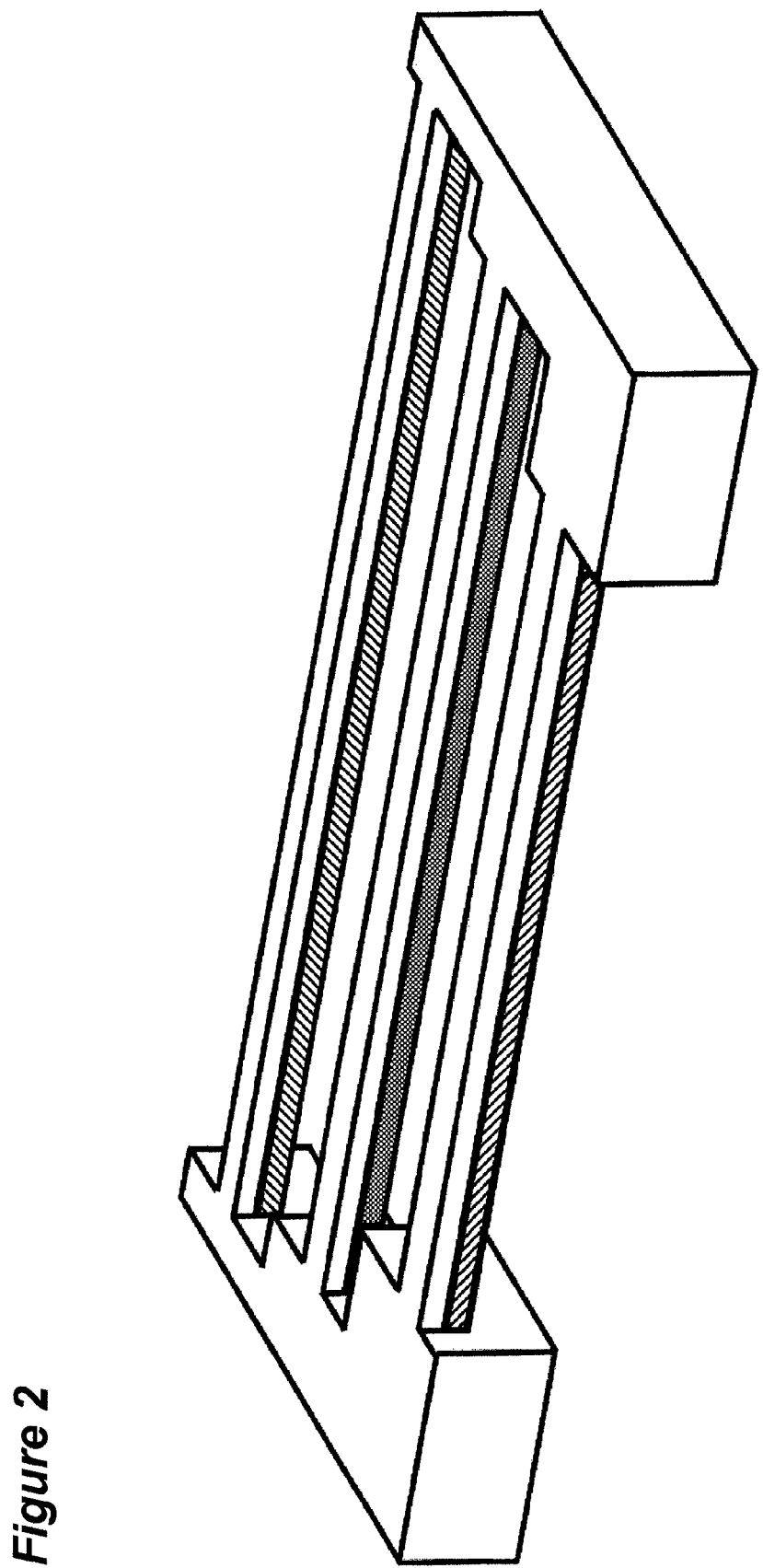
FIG. 2 shows a sensing device according to one embodiment comprising an array of doubly-clamped bi-layered composite beam-shaped geometric structures of varying length.

The embodiments can be easily multiplexed into an array of detectors. They can be arranged in a square, for example of 4×4 sensors or 10×10 sensors, in a rectangular shape, for example of 2×4 sensors or 10×20 sensors, circular, or any other shape that may be useful. The spacing of such arrays is often limited for systems that utilize optical measurement techniques due to alignment and spot size considerations, while the design proposed here presents no such limitation, allowing for a high concentration of devices to be integrated in a small area. Various beam-shaped structures can for instance be coated with different gas adsorption/absorption layers, such as to make them sensitive to different gases or to allow for identification of a specific gas by analyzing the collective response at a specific time. FIG. 2 shows a small section of the possible layout of individually coated resonators in a row, of varying dimensions. Additionally, it is possible to construct beams with identical materials and lateral dimensions but varying layer thicknesses and compare the responses from each beam to extract additional information (e.g. diffusion time, concentration). Each beam can also be coated with multiple materials (like shown in FIG. 1(b) to achieve sensitivity towards multiple analytes at the same time without distinguishing among them. In another embodiment, devices of identical dimensions but different absorbent layers can be fabricated to gain different sensitivities towards varying analytes for distinguishing among analytes. The beam array approach allows for the identification of complex vapor mixtures, such as odors, which generate a unique signature of signals on appropriately coated resonator arrays. Due to the compactness and simplicity of the embodiment, such arrays can be easily integrated into low-power autonomous sensor nodes.

The above-described array approach also allows for the compensation of undesired environmental effects, through the use of one or more reference resonators that are engineered to be unresponsive to the analyte of interest but only responsive to effects that need to be cancelled (e.g. changes in temperature, pressure) by selection of appropriate material combinations. The reference resonators can be made without any coating (i.e. single homogenous structural layer) if the structural layer is sufficiently responsive to the environmental effect to be eliminated or with multiple layers where the layers are known to either not absorb or not swell in response to absorption of the target analyte(s) but only to environmental variations. The reference resonator will, preferably, be fabricated in close proximity to the sensing resonator with identical fabrication steps. During operation of the sensing device, the difference in the observed changes of resonance characteristics (e.g. modal frequency, quality factor) of the sensor resonator(s) and reference resonator(s) will be indicative of the effect of the analyte. The differences can be identified by embedding the sensing and reference resonators in a single integrated circuit where, for example, the modal frequency difference is directly read-out. Performing a differential read-out can result in lower power consumption while the use of sensor elements of the same type (i.e. multi-clamped resonators) will result in easier integration, lower fabrication costs and smaller form factor. The close proximity of the reference element to the sensing element that is achievable in the array configuration will also ensure that the measured difference is solely due to the target analyte.

Each beam can be connected to electronics and/or software that allow identification of a specific gas concentration from a shift in resonance frequency. Therefore, electrodes can be included in or on the sensor(s), connected to measurements and actuation electronics, for example via the clamps and a structure supporting the sensor(s). The electrodes can be made of metals as for example Au, Cu, Al, Pt, W, Ir, or a combination thereof, conductive oxides such as $IrO_2$, $SrRuO_3$, $RuO_2$, indium tin oxide or conductive nitrides as TiN, TaN. The integrated electronics can consist of one or more detectors, for example displacement detector(s) as well as one or more actuators to induce structural motion for realizing vibration at a resonance frequency, at the fundamental or higher vibration mode of the structure. The transducers can be placed on any interface. The actuator can be a part of the displacement measurement transducer or it can be separately located, preferably at another clamp. Separation of the actuator and detector can allow for enhanced precision in detecting structural vibrations.

The vibration detector and actuator subsystems can be constructed using piezoelectric, piezoresistive, optical, magnetoelectric or magnetostrictive materials, patterned appropriately on the suspended structure. In one embodiment, a piezoelectric actuator patch, with a piezoelectric material sandwiched between two conductive layers is deposited at one clamping end. The patch can be made from lead zirconium titanate (PZT), zinc oxide (ZnO) or aluminum nitride (AlN) as well as piezoelectric polymers (such as polyvinylidene fluoride (PVDF)). The conductive layers can be made from any low-resistance metal (e.g. platinum, gold, aluminum, copper, tungsten, titanium), conductive oxide or nitride, or doped silicon patch. Using the conductive electrode layers, a harmonic voltage difference can be applied across the piezoelectric material to generate beam vibrations. In another approach, the piezoelectric patch can be used for generating voltages based on existing vibrations or in a combined actuation/detection (one-port readout) configuration with appropriate signal processing circuit. In another embodiment, piezoresistive displacement detection can be performed by using thin wires, preferably in loop formation patterned from metals or doped semiconductors. The resistance of the wire can change as result of the motion of the beam due to strain formation at the clamp and the wire. A bias voltage or current can be applied to measure the resistance change. Appropriate bridge circuitry can be integrated on the same chip to provide differential signal output as a function of a single resonator vibration by eliminating the initial resistance. The bridge configuration can also be extended to include piezoresistors from multiple resonators to perform direct differential measurement that eliminates the above-mentioned environmental effects or to gain selectivity.

Figure 3:
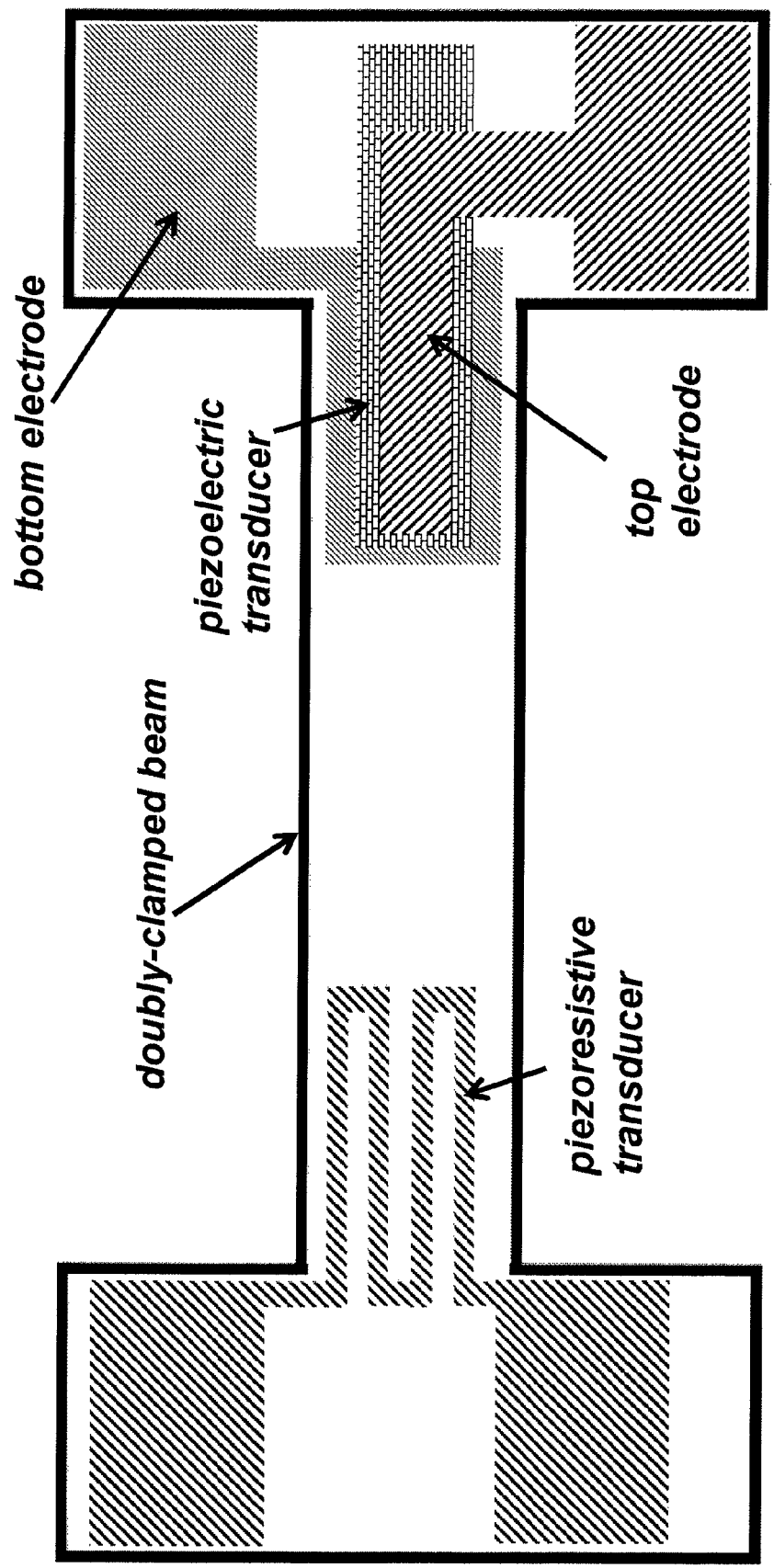
FIG. 3 shows a top view of a sensing device with piezoresistive and piezoelectric transducers and their electrical connections.

The advantage of having two or more separate clamps can be further exploited to integrate two or more separated transducers, one in each clamp. The split approach will allow for decoupling of the actuation and sensing mechanisms, providing lower cross-talk between the transduction scheme, improving signal-to-noise levels and enabling higher sensitivity. A typical layout is displayed in FIG. 3, where piezoresistive and piezoelectric transducers are embedded at opposite clamping regions. Optimum performance can be achieved by extending and patterning the transducers over the suspended region according to the shape of the resonance mode used for operation. Multiple transducer patches can be placed on the resonator, according the desired resonant operation mode shape(s) to enhance the electrical signal.

Using the actuation and detection transducers, measurement of the resonance characteristics can be performed by sweeping actuation frequency and recording response amplitude to determine peak response frequency (i.e. resonance frequency) or resonance frequency bandwidth (i.e. quality factor of resonance mode), or by fixing the actuation frequency at an optimized level and recording the change in amplitude of response or its phase. Further enhancements to the sensitivity can be obtained using specialized frequency tracking circuitry like phase-lock loops (PLL) or frequency counters or by embedding the resonator into an oscillator circuit configuration. To minimize power consumption, the actuation can, in certain applications, be eliminated and only the thermomechanical self-vibrations of the device can be monitored using any one of the above mentioned transduction schemes.

The sensor can be made on a wafer (silicon, silicon on insulator, silicon nitride, quartz, gallium arsenide, among others) of desired properties. The fabrication can be performed on a silicon wafer (for example 150 mm diameter, 670 micron thickness), with low doping level (high resistivity). In case of silicon-on-insulator (SOI) wafers, the thicknesses of the buried sacrificial oxide and device layer can be adjusted according to the desired device characteristics and fabrication limitations, with typical thicknesses in the 100 nm-500 nm range. Crystal orientation of the device layer can be selected according to desired mechanical elasticity or fabrication steps. If starting with single material wafer, individual layers can be deposited for sacrificial etching (e.g. silicon oxide which can be selectively etched using hydrofluoric acid solutions) and forming the device layer (e.g. silicon, silicon nitride, silicon carbide). Additionally, depositions of the piezoelectric material, (AlN, PZT, ZnO, PVDF, etc.) and the electrode layers for transduction and signaling (conductive films like Au, Pt, Al, W etc.) can be performed. The patterning can be achieved using consecutive steps of standardized semiconductor fabrication techniques of lithography and etching in a top-down approach. Also, lift-off can be used, or layer depositions and etching processes can be suitably interchanged to obtain a similar stack. Once the device pattern and the overlaying circuitry are completed, the structure can be released by etching through the wafer from the backside, allowing access to both the top and bottom surfaces of the resonator. At this stage, the structure surface to be later coated can be nanostructured with grooves or holes, as described above. Individual devices can be coated on the back and/or front side with absorbent polymer using spraying, ink-jet printing (drop-on-demand), microspotting, dipping or spin-coating. In the preferred ink-jet printing approach, a small nozzle can be approached to individual suspended beams and droplets of the dissolved polymer (or ionic liquid) solution can be placed on the doubly-clamped beam with desired volume and placement. The use of inkjet printing for coating of individual structures allows for an accurate control of the coating layer through adjustment of the solution concentration, drop diameter and number of drops on the device. As such, adjacent devices in the above mentioned array configuration can be coated with different absorptive chemicals. The devices can be baked to remove the solvent and harden the polymer (or ionic liquid) coating. The completed device can be embedded into appropriate packaging which allows for analyte flow and signaling.

The micromechanical sensor array prepared with the above described methods can be integrated into a controlled flow environment and an advanced circuitry allowing for comparative measurement of each individual sensor beam. The frequency response of individual beams can be measured, preferably around their resonance frequencies, at one or more natural modes of the devices. The resonance can be determined by the amplitude of motion and/or the phase change in the actuation-detection signal line. The response signal can be enhanced for each beam through sufficient actuation, preferably piezoelectrically. The sensitivity of individual resonators can be further enhanced by feedback circuitry, or locked frequency tracking.

A change in the concentration of an analyte in the vicinity of the resonator will result in an increase or decrease in the resonance frequency of an individual beam. The amplitude of oscillation will be most prominent in the fundamental resonance mode depicted in FIG. 2, however higher order modes can demonstrate a larger differential signal, higher quality factor and/or higher signal to noise level, resulting in a greater sensitivity for the analyte detection. Comparative processing of the response signals from different devices can be performed to obtain signature responses that are matched against previous calibration tests, allowing the sensor node to identify the occurring changes in its environment.

Experiment 1

The sensor can be made and tested as follows. On a 6 inch silicon wafer of 675 μm thickness with resistivity 1-100 Ohm-cm and <100> crystal orientation, a sacrificial etch layer of 500 nm silicon oxide and a structural device layer of 500 nm thick silicon nitride is deposited. On top of this stack, an electrical contact and piezoresistive wiring layer of 100 nm of platinum, and a piezoelectric transducer layer of aluminum nitride (e.g. 400 nm thick) is deposited. Finally, a top electrical contact of 100 nm of platinum for transduction and signaling is deposited. The electrical contacts, the piezoelectric transducer and the piezoresistive strain gauge are consecutively patterned using standard lithography and etching methods in a top-down approach. Beams of a range of widths (1-100 μm) and lengths (25-750 μm) are patterned in parallel on a single wafer using lithography and etching of silicon nitride structure layer. In a next process, the structure is released by etching through the wafer from the backside. The resulting silicon nitride beams have a width of 1-100 μm and a thickness of 500 nm in regions not containing transducer elements.

Figure 5A:
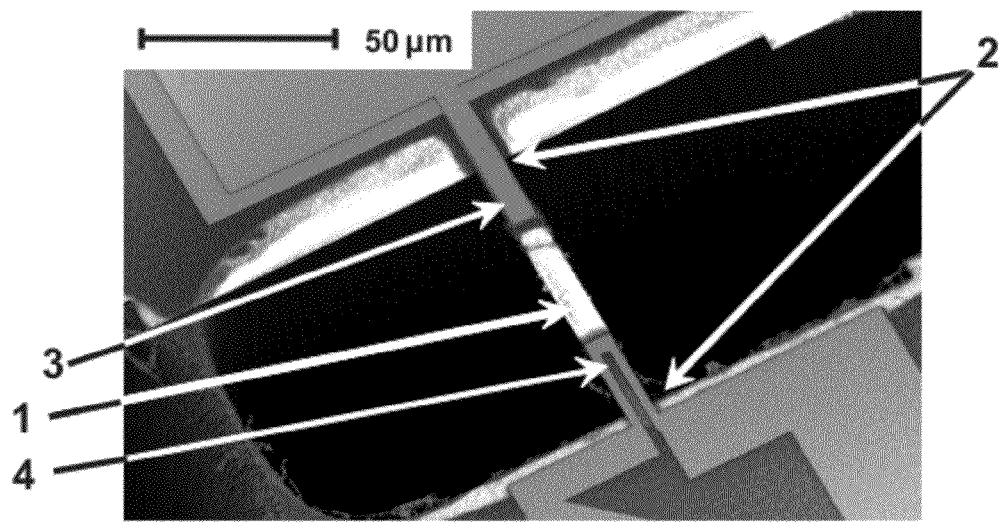
FIG. 5 shows a scanning electron microscope image of (a) a single doubly-clamped suspended beam resonator (b) an array of doubly-clamped resonators, with identical thickness and width and varying length.
Figure 5B:
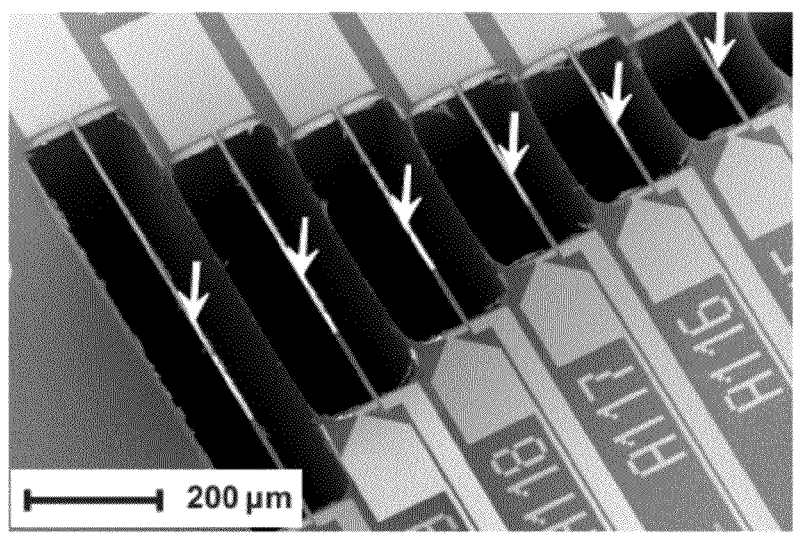

The scanning electron microscope pictures of exemplary devices, fabricated using the above described procedure, are shown in FIGS. 5(a) and 5(b). In FIG. 5(a), a suspended beam 1, fabricated from silicon nitride with dimensions of 500 nm thickness, 110 μm length and 8 μm width, is supported by clamps 2 at both ends. Piezoelectric 3 and piezoresistive transducers are integrated at opposite clamping ends. In FIG. 5(b), an array of suspended doubly-clamped beams (each indicated by the arrow) with identical thickness and width but varying length are displayed. The longer beams demonstrate the feasibility of very high aspect (length/thickness) ratios, as high as 1500.

The sensor area is subsequently coated on the backside with approximately 1 μm of polyvinylpyridine (PVP) using inkjet printing for the detection of ethanol vapor. The devices can then be heated to 120° C. to remove solvent(s) and harden the polymer coating.

The device is then electrically wirebonded in a chip package, placed in a testing chamber with gas flow control capabilities and connected to circuit analysis tools for characterization. The device is kept at room temperature throughout the characterization process. The resonance characteristics of the devices are recorded using frequency sweeping of the impedance of the piezoelectric patch or alternately through monitoring of the resistance of the piezoresistive patch while the piezoelectric actuator frequency is swept.

Figure 6A:
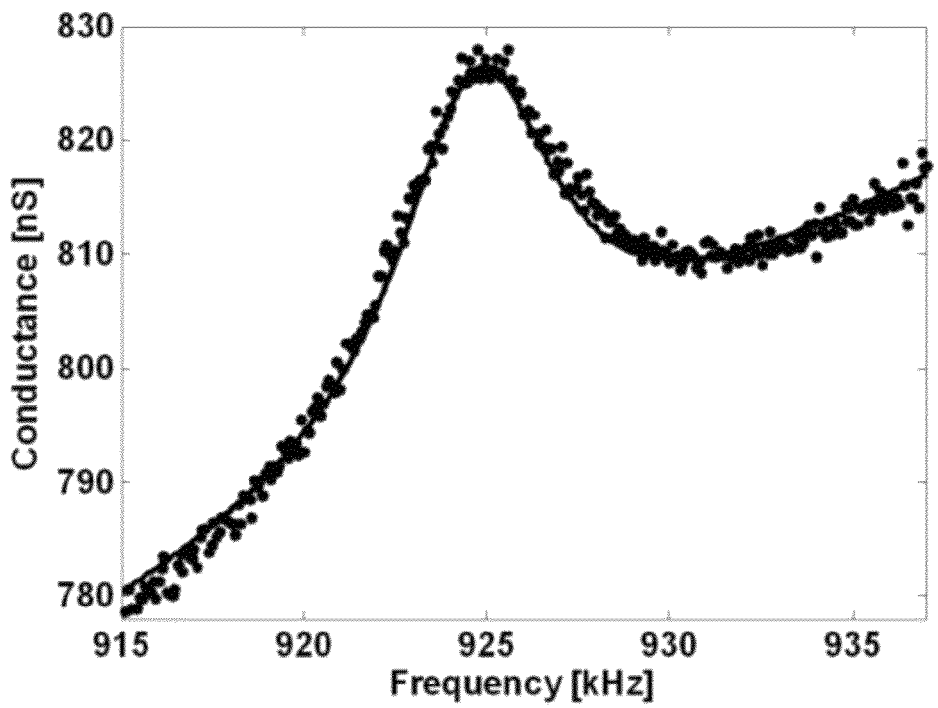
FIG. 6($a$) shows the frequency response characteristics of a doubly-clamped suspended silicon nitride beam resonator, with dimensions of 500 nm thickness, 100 μm length and 70 μm width, measured by one-port multi-frequency characterization of the integrated piezoelectric transducer, with 0.25 V ac voltage and zero biasing.

FIG. 6(a) shows the frequency response characteristics of a doubly-clamped suspended silicon nitride beam resonator, with dimensions of 500 nm thickness, 100 μm length and 70 μm width, measured by one-port multi-frequency characterization of the integrated piezoelectric transducer, with 0.25 V ac voltage and zero biasing. The measurement is performed at room temperature and atmospheric pressure and the quality factor of the device is determined to be Q~170 under these conditions.

Figure 6B:
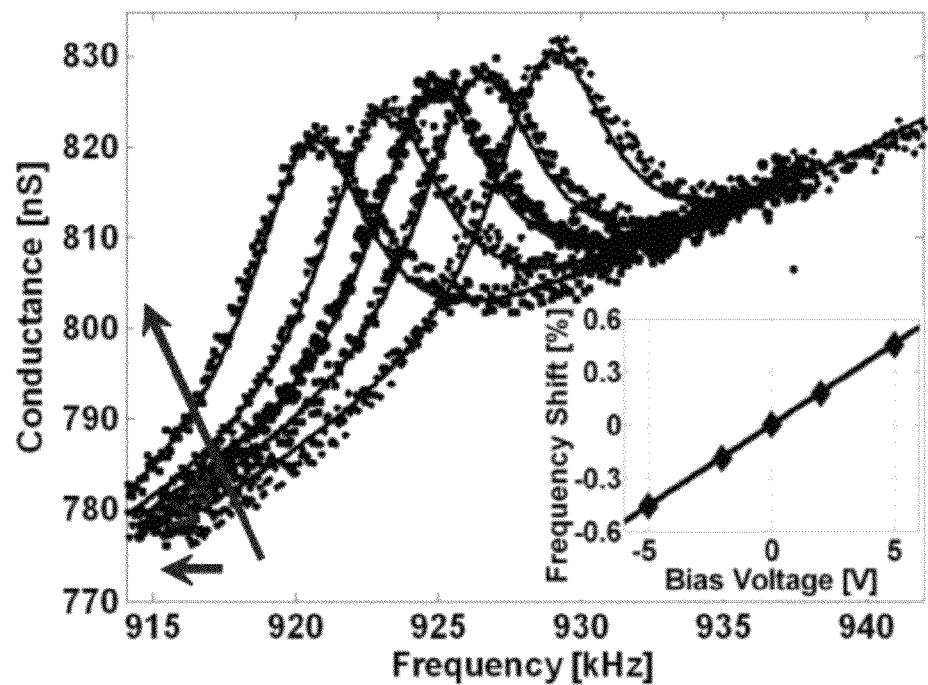

The proposed mechanism of stress-induced resonance frequency shift is demonstrated in the measurements displayed in FIG. 6(b). Here, the piezoelectric patch of the device described in FIG. 6(a) is biased with varying dc voltage, essentially generating partial stress formation in the doubly-clamped beam, and the resonance peak is observed to shift linearly, as shown in the inset.

In order to demonstrate the same response mechanism as a result of analyte absorption in the polymer layer, the experiment is repeated during various gas compositions ranging from pure nitrogen to nitrogen with ethanol vapor saturation, to determine the frequency shift response as a function of ethanol vapor presence. Additionally, the experiment is repeated in the presence of different vapors, like methanol, toluene, oxygen and water (humidity), to determine the response selectivity of the polymer. The chamber conditions are also alternated in a cyclic fashion to determine the sensor response repeatability and reversibility.

Experiment 2

An analytical solution to the dependence of the resonance frequency on stress formation was obtained by using the beam theory through appropriate adaptations to account for the composite layering of the proposed device. The resonance frequency $f_n$ of vibration mode n of a doubly-clamped beam was approximated from $$f_n = \frac{\beta_n^2}{2\pi}\sqrt{\frac{E_c I_c}{\rho_c A_c}}, \quad (1)$$

where $E_c$ and $\rho_c$ are the effective modulus of elasticity and density, respectively, of the composite structure, $I_c = w h_c^3/12$ is the moment of inertia, $A = w h_c$ is the cross-sectional area for a beam of width w and total thickness $h_c$. Here, $\beta_n$ is the modal coefficient which is equal to $\beta_0 = 4.73$ μL for the fundamental mode (n=0) of a beam of length L. The dependence of the fundamental resonance frequency on length L and aspect ratio $L/h_{Si}$ is plotted in FIG. 5, for a silicon-PMMA composite beam where the thickness ratio of the composite layer is $h_{PMMA}/h_{Si} \sim 1.7$.

A swelling effect in the polymer layers creates a compressive ($\sigma<0$) stress in the structure. The magnitude of the stress is proportional to the modulus of elasticity of the polymer layer $E_P$ and the longitudinal strain $\epsilon_L$ induced by absorption $$\sigma = \epsilon_L E_P \quad (2)$$

The resonance frequency of a doubly-clamped beam under bulk stress σ in the polymer layer was analytically described as $$\frac{\omega_\sigma}{\omega_0} = \sqrt{1 + \frac{\sigma A_\sigma L^2}{4\pi^2 E_c I_c}}. \quad (3)$$

Figure 7:
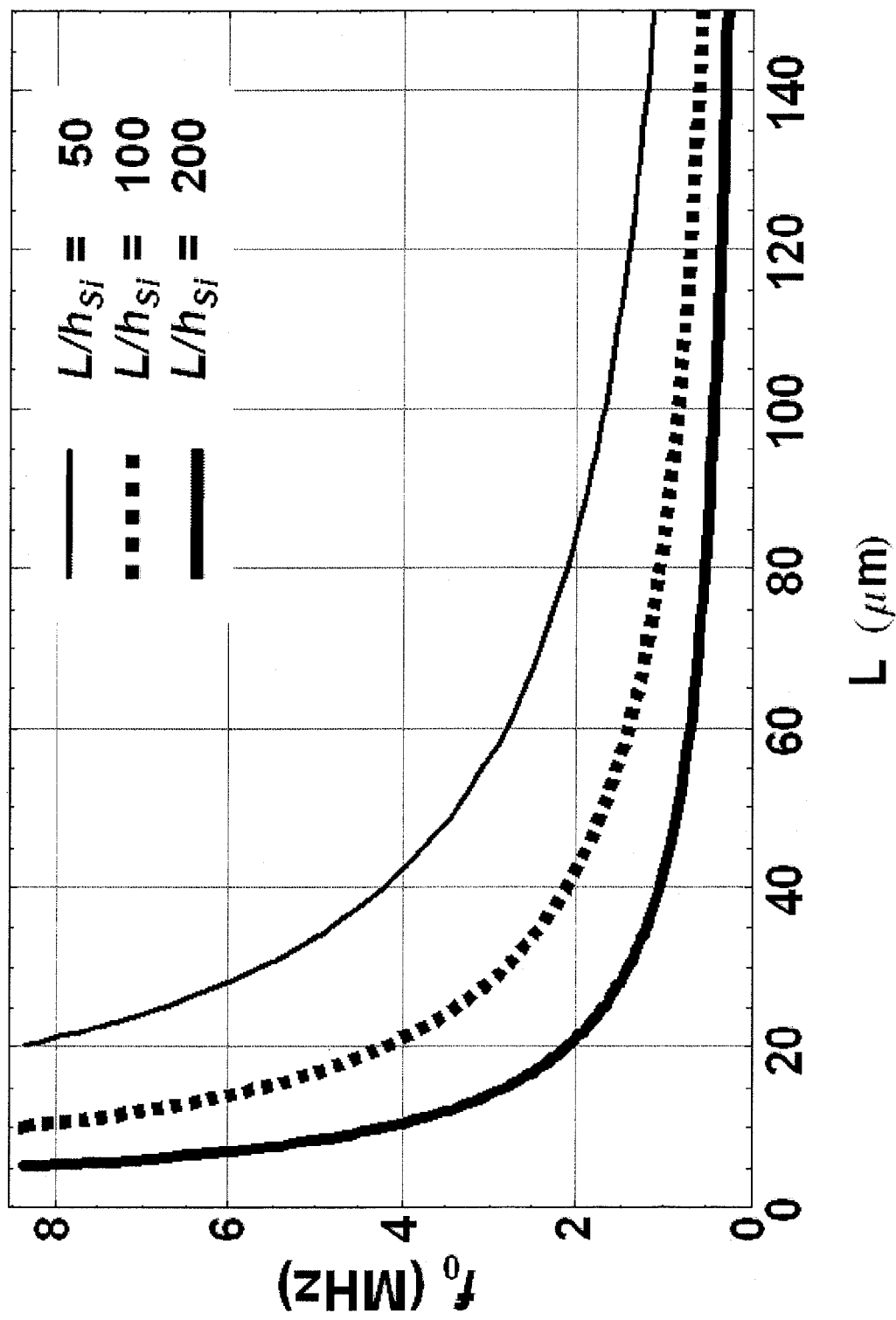
FIG. 7 shows a fundamental resonance frequency $f_0$ of a composite doubly-clamped resonator as a function of length L, for varying aspect ratio $L/h_{Si}$ at a constant thickness ratio $h_{PMMA}/h_{Si} \sim 1.7$.

Here, $A_\sigma$ is the cross-sectional under stress, which in this case was taken as the polymer layer, $A_\sigma = h_P w$. A numerical confirmation of these approximations was obtained from finite element modeling of the structure. Both numerical and analytical stress analysis of the doubly-clamped geometry yielded results that indicate a fundamental mode responsivity levels of R~20 (% frequency shift % volume change) for the specific geometry analyzed here, as represented in FIG. 7. This response will be in addition to the mass-induced inertial response of the device, which can be on the order of 10 Hz/ag.

It is clear from Eq. 3 that the responsivity of the doubly-clamped resonator to stress formations is highly dependent on device geometry as well as mechanical characteristics of the layers. Hence, an optimization is necessary to maximize response signal for a specific stress formation. The figure of merit for comparison of device performance can be defined as responsivity of normalized frequency shift to stress formation $R_\sigma$. Using Eq. 3, this responsivity can be expressed as $$R_\sigma = \frac{1}{\omega_0}\frac{\partial \omega_\sigma}{\partial \sigma} = \frac{A_\sigma L^2}{8\pi^2 E_c I_c}\left[1 + \frac{\sigma A_\sigma L^2}{4\pi^2 E_c I_c}\right]^{-\frac{1}{2}}. \quad (4)$$

Figure 8:
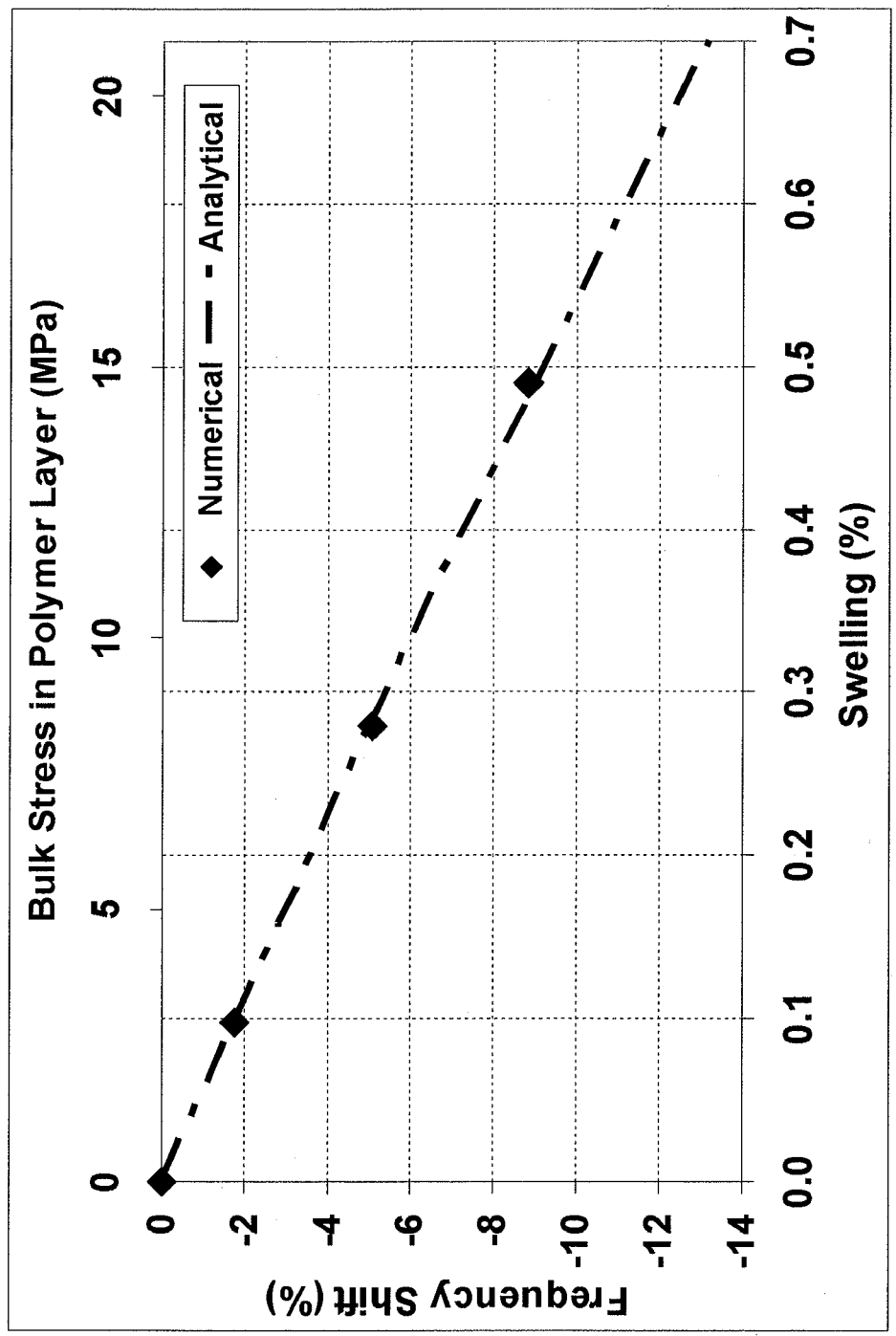
FIG. 8 shows a stress-induced resonance frequency shift in a doubly-clamped resonator with dimensions ($h_{Si} \times W \times L$) 0.1 μm×6 μm×20 μm and polymer (PMMA) coating of $h_{PMMA}=0.9$ μm.
Figure 9A:
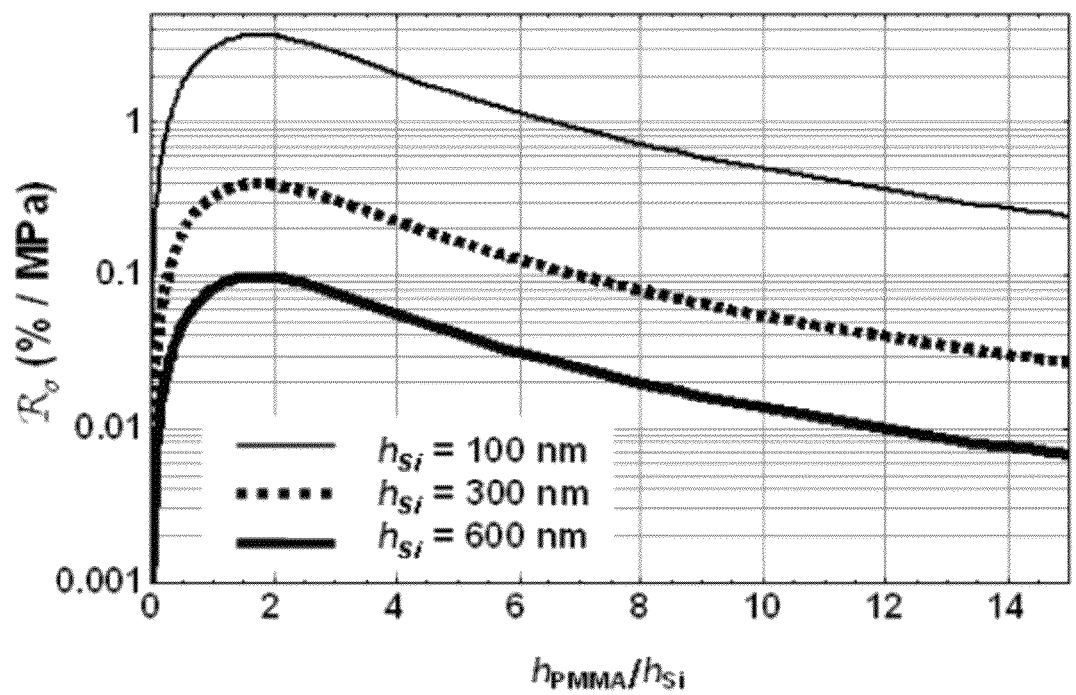
FIG. 9 shows a stress-responsivity $R_\sigma$, of a doubly-clamped resonator at a compressive stress level of σ=1 MPa for (a) a device with dimensions (w×L) 6 μm×20 μm, as a function of layer thickness ratio $h_{PMMA}/h_{Si}$, for varying silicon layer thickness $h_{Si}$ values, and (b) showing the length and aspect ratio dependence of stress-responsivity.
Figure 9B:
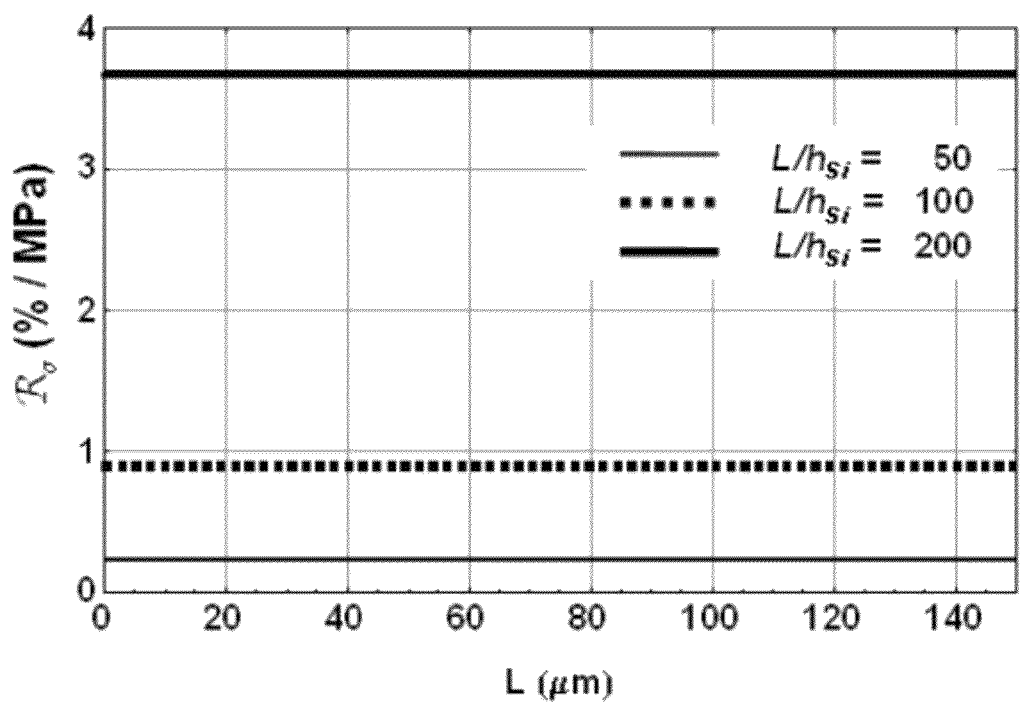

The most easily tunable parameter governing the responsivity of nanomechanical resonators to environmental changes is the geometry of the device. The geometric analysis results, presented in FIG. 8(a), lead to the conclusion that an optimization of the layer thickness ratio of the polymer and the structural layer can improve this result significantly, such that a ratio of $h_{PMMA}/h_{Si}$~0.7 provides the optimum result when using PMMA-silicon composite beams.

The frequency responsivity to stress was determined to be independent of the length L of the doubly-clamped resonator, for a clamped beam resonator of uniform thickness, as displayed in FIG. 7(b). Instead, for the proposed design, the critical design parameter was the aspect ratio ($L/h_{Si}$), such that increasing $L/h_{Si}$ was determined to improve device responsivity to stress formation, as indicated in FIG. 7(b). Nonetheless, the length of the resonator determined the operation frequency of the device according to results presented in FIG. 5 for different aspect ratio beams. As such, the proposed design allows for a very tunable sensor, whose frequency can be selected as desired while maintaining sensitivity. The selection criteria for the frequency can be based on the electronic components like the signal analysis circuitry, but will preferably be in the kHz-MHz regime.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A sensing device for detecting an analyte, the device comprising:
    at least one geometrical structure comprising a peripheral edge;
    at least one chemical responsive layer being absorbent or adsorbent for the analyte; and
    at least two clamps by which the peripheral edge of the at least one geometrical structure is partially clamped on at least two opposite sides,
    wherein the at least one chemical responsive layer has a varying effective spring constant which changes upon absorption or adsorption of the analyte, wherein the at least one chemical response layer comprises a first and a second chemical responsive layer on opposite sides of the at least one geometrical structure, wherein the first and second chemical responsive layers are absorbent or adsorbent for different analytes.

2. The sensing device according to claim 1, further comprising:
    an actuation system configured to realize vibration of the at least one geometrical structure at a resonance frequency of the geometrical structure; and
    a detection system configured to detect a shift in the resonance frequency of the geometrical structure upon absorption or adsorption of the analyte.

3. The sensing device according to claim 2, wherein the actuation system is integrated in one of the at least two clamps and the detection system is integrated in another of the at least two clamps.

4. The sensing device according to claim 1, wherein the at least one geometrical structure comprises a support structure on which the at least one chemical responsive layer is provided.

5. The sensing device according to claim 4, wherein the support structure is structured at its interface with the at least one chemical responsive layer with microscale and/or sub-micronscale grooves or holes.

6. The sensing device according to claim 5, wherein the microscale and/or sub-microscale grooves extend in a direction perpendicular to a longitudinal axis of the geometrical structure.

7. The sensing device according to claim 1, wherein the at least one chemical responsive layer has a varying volume upon absorption or adsorption of the analyte.

8. The sensing device according to claim 1, wherein the at least one chemical responsive layer has a varying flexural rigidity upon absorption or adsorption of the analyte.

9. The sensing device according to claim 1, wherein the at least one chemical responsive layer has a varying mass upon absorption or adsorption of the analyte.

10. The sensing device according to claim 1, wherein the at least one chemical responsive layer comprises a polymer.

11. The sensing device according to claim 1, wherein the geometrical structure is a beam-shaped structure clamped at two opposite ends.

12. The sensing device according to claim 1, wherein the geometrical structure is a cross-shaped structure clamped at four ends.

13. The sensing device according to claim 1, wherein the geometrical structure is an H-shaped structure clamped at four ends.

14. The sensing device according to claim 1, wherein the geometrical structure has a main axis and is clamped exclusively on opposite ends of the main axis, such that most of the peripheral edge is left free to vibrate.

15. The sensing device according to claim 1, wherein the sensing device comprises a plurality of the geometrical structures.

16. The sensing device according to claim 15, wherein the chemical responsive layers of at least two of the plurality of geometrical structures are absorbent or adsorbent for different analytes.

17. The sensing device according to claim 1, wherein the sensing device further comprises a reference geometrical structure which is substantially not responsive to the analyte.

18. A method of making a sensing device for detecting an analyte, the method comprising:

provide at least one geometrical structure comprising a peripheral edge;

providing at least one chemical responsive layer being absorbent or adsorbent for the analyte; and forming at least two clamps by which the peripheral edge of the at least one geometrical structure is partially clamped on at least two opposite sides, wherein the at least one chemical responsive layer has a varying effective spring constant which changes upon absorption or adsorption of the analyte, wherein the at least one chemical response layer comprises a first and a second chemical responsive layer on opposite sides of the at least one geometrical structure, wherein the first and second chemical responsive layers are absorbent or adsorbent for different analytes.

* * * * *